(12) United States Patent
Gonterman

(10) Patent No.: US 9,278,207 B2
(45) Date of Patent: Mar. 8, 2016

(54) COSMETOLOGY DEVICE

(71) Applicant: Wayne D. Gonterman, Mountain View, CA (US)

(72) Inventor: Wayne D. Gonterman, Mountain View, CA (US)

( * ) Notice: Subject to any disclaimer, the term of this patent is extended or adjusted under 35 U.S.C. 154(b) by 0 days.

(21) Appl. No.: 14/061,540

(22) Filed: Oct. 23, 2013

(65) Prior Publication Data
US 2015/0112417 A1    Apr. 23, 2015

(51) Int. Cl.
*A61N 1/00* (2006.01)
*A61N 1/04* (2006.01)
*A61N 5/06* (2006.01)
*A61H 23/00* (2006.01)
*A61F 7/00* (2006.01)
*A61M 35/00* (2006.01)
*A61N 1/32* (2006.01)

(52) U.S. Cl.
CPC ............... *A61N 1/0472* (2013.01); *A61F 7/00* (2013.01); *A61F 2007/0052* (2013.01); *A61F 2007/0071* (2013.01); *A61F 2007/0075* (2013.01); *A61F 2007/0087* (2013.01); *A61H 23/00* (2013.01); *A61M 35/003* (2013.01); *A61N 1/328* (2013.01); *A61N 5/06* (2013.01); *A61N 5/0616* (2013.01)

(58) Field of Classification Search
USPC .......................................... 607/148
See application file for complete search history.

(56) References Cited

U.S. PATENT DOCUMENTS

| 5,051,259 A | 9/1991 | Olsen et al. | |
| 2011/0118722 A1* | 5/2011 | Lischinsky et al. | 606/33 |
| 2012/0065575 A1 | 3/2012 | Loenardi Kader | |
| 2012/0197249 A1* | 8/2012 | Leyh et al. | 606/34 |

FOREIGN PATENT DOCUMENTS

CN    101869739 A    10/2010

* cited by examiner

*Primary Examiner* — Robert N Wieland
(74) *Attorney, Agent, or Firm* — Mintz Levin Cohn Ferris Glovsky and Popeo, P.C.

(57) ABSTRACT

A device for applying electrical stimulation to a surface of the human body utilizes a calibrated, pre-arranged pattern of conducting, current emitting elements to distribute current throughout an entire surface at once, such as human face, without needing to alter the device to accommodate various are sizes, including varying face sizes.

23 Claims, 8 Drawing Sheets

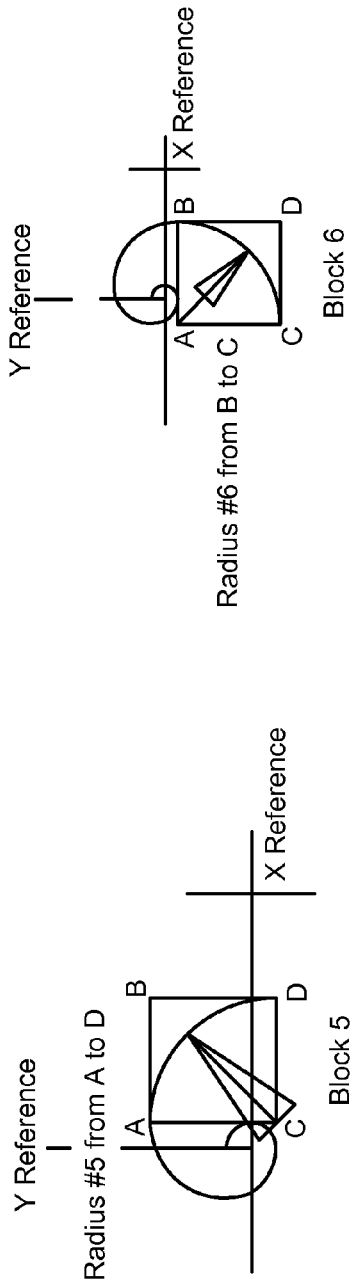
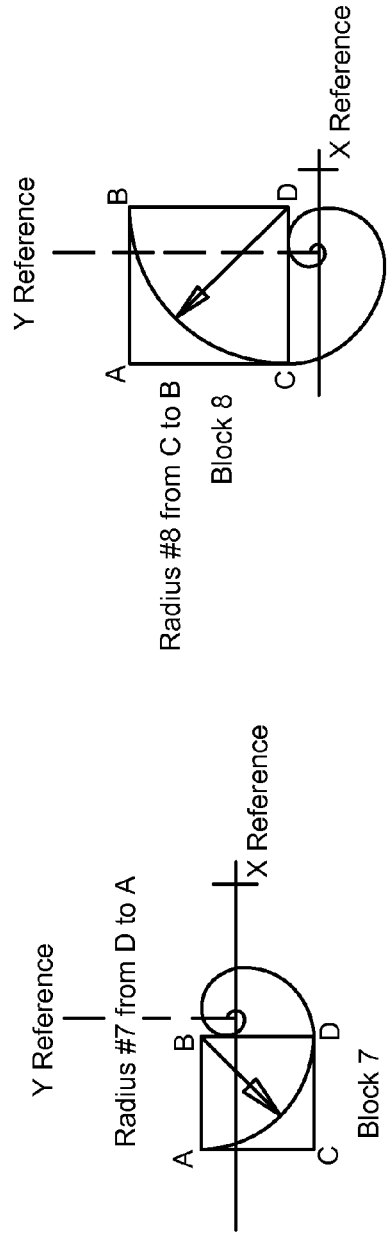
FIG. 2E
FIG. 2F
FIG. 2G
FIG. 2H though other means of electrical contact; an outer contact point in electrical contact with a perimeter contact ring that is situated along the circumference of the cosmetology device; and a plurality of conducting elements, each conducting element extending across a working surface of the cosmetology device, wherein: a first end of each conducting element contacts a first point on the perimeter contact ring; a second end of each conducting element contacts a second point on the perimeter contact ring; and a midpoint of each conducting element contacts the center contact line.

COSMETOLOGY DEVICE

TECHNICAL FIELD

The subject matter described herein relates to devices, systems, and methods for applying electrical current to the surface of a part of the human body, such as the face.

BACKGROUND

The application of low levels of electric current has been used for physical therapy, including for producing favorable changes in appearance. In current systems for applying current to the human body, typically pairs of electrodes are employed, either as point to point electrodes or as electrical pads. Conduction of electrical current from the systems currently employed to the surface of the body to be treated usually require a conductive means, such as a gel or pads, to pass current from the electrodes to the area of interest on the body. To cover large areas of the body using current systems, the electrodes need to be moved around manually, or multiple pairs of electrodes must be placed manually over the area to be treated.

SUMMARY

In one aspect, there is provided an apparatus. The apparatus may include a proximal end contact point; a distal end contact point; and a plurality of spiral conducting elements radiating from an outer ring including the distal end contact point to a central region including the proximal end contact point, wherein each of the plurality of spiral conducting elements includes a tip portion electrically coupled to the proximal end contact point, and wherein each of the plurality of spiral conducting elements includes a base portion electrically coupled to the outer contact ring to form at least one electrical circuit configured to carry a micro-current.

In some variations one or more of the features disclosed herein including the following features can optionally be included. Each of the plurality of spiral conducting elements may be offset from an adjacent spiral conducting element by a predetermined angle. Each of the plurality of spiral conducting elements may be offset from an adjacent spiral conducting element by an angle of about 222.5°. The plurality of conducting elements may include two or more conducting elements. The plurality of conducting elements may include at least one of a logarithmic spiral, an Archimedean spiral, a hyperbolic spiral, and a spiral having a curved structure which winds around a fixed center point at a continuously increase or decreasing distance from the proximal end contact point. A fabric outer layer may be attached onto the plurality of conducting elements. The cosmetology device may include a working surface, the working surface including the plurality of conducting elements. The working surface may be configured to contact a subject's face or other tissue to be treated. The plurality of conducting elements may include at least one of a conductive tape, a conductive thread, a conductive yarn, a conductive paint, or a wire. The apparatus may include a power source and a controller in electrical contact with the center contact point and the outer contact point. The plurality of conducting elements may include substantially straight lines, when the working surface is flat. The plurality of conducting elements may be aligned in one direction and are substantially parallel to each other. The plurality of conducting elements are arranged in a grid pattern.

In another aspect, there is provided an apparatus. The apparatus may include a center contact line connected to a first In some variations one or more of the features disclosed herein including the following features can optionally be included. The apparatus may include a second center contact line. The working surface may include a fabric outer layer onto which the plurality of conducting elements are attached. The working surface may be configured to contact a subject's face or other tissue to be treated. The plurality of conducting elements may include wire comprising copper, aluminum, other conducting material, or any combination thereof. The apparatus may include a power source and controller in electrical contact with the center contact point and the outer contact point.

In another aspect, there is provided a method. The method may include applying, to a portion of a face, a device for treating the portion, wherein the device includes a center contact point; an outer contact point; and a plurality of spiral conducting elements radiating from an outer ring including the outer contact point to a central region including the center contact point, wherein each of the plurality of spiral conducting elements includes a tip portion electrically coupled to the center contact point, and wherein each of the plurality spiral conducting elements includes a base portion electrically coupled to the outer contact ring to form at least one electrical circuit configured to carry a micro-current into a cosmetology device; and energizing the device to allow energy to radiate into the portion of the face.

In a related aspect, a method is provided that includes applying a device for treating a portion of a face and energizing the device to allow energy to radiate into the portion of the face. The device can include a proximal end contact point; a distal end contact point; and multiple spiral conducting elements. In such methods, each spiral conducting element can form at least one electrical circuit configured to carry a micro-current into a cosmetology device.

Implementations of the current subject matter can include, but are not limited to, systems and methods consistent including one or more features are described as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIGS. 2A-2L show how the calculation of an exemplary pattern for use with a device disclosed herein.

When practical, similar reference numbers denote similar structures, features, or elements.

DETAILED DESCRIPTION

In some example implementations, there is provided a cosmetology device providing therapeutic amounts of electrical stimulation, in the form of electrical current, over an area of the surface of the human body. For example, the device may be placed over the face to stimulate the face, providing thus a beneficial stimulation to the face.

In some example implementations, the application of electrical current may provide one or more benefits, such as speeding recovery from injury, over-exertion, and/or the like. In the case of the skin, particularly that of the face, electrical current on the order of micro-amps may be used to improve the appearance of the skin by reducing wrinkles, lessening the presence or severity of acne, improving the circulation of the vasculature and lymphatic system components in the treated areas, and/or other therapeutic effects as well.

Although some of the examples described herein refer to applying electrical currents to stimulate the face, other parts of the body may be used as well. Moreover, although some of the examples described herein refer to applying electrical currents to a human, other animals may be subject to the electrical currents provided by the cosmetology device disclosed herein.

Figure 1A:
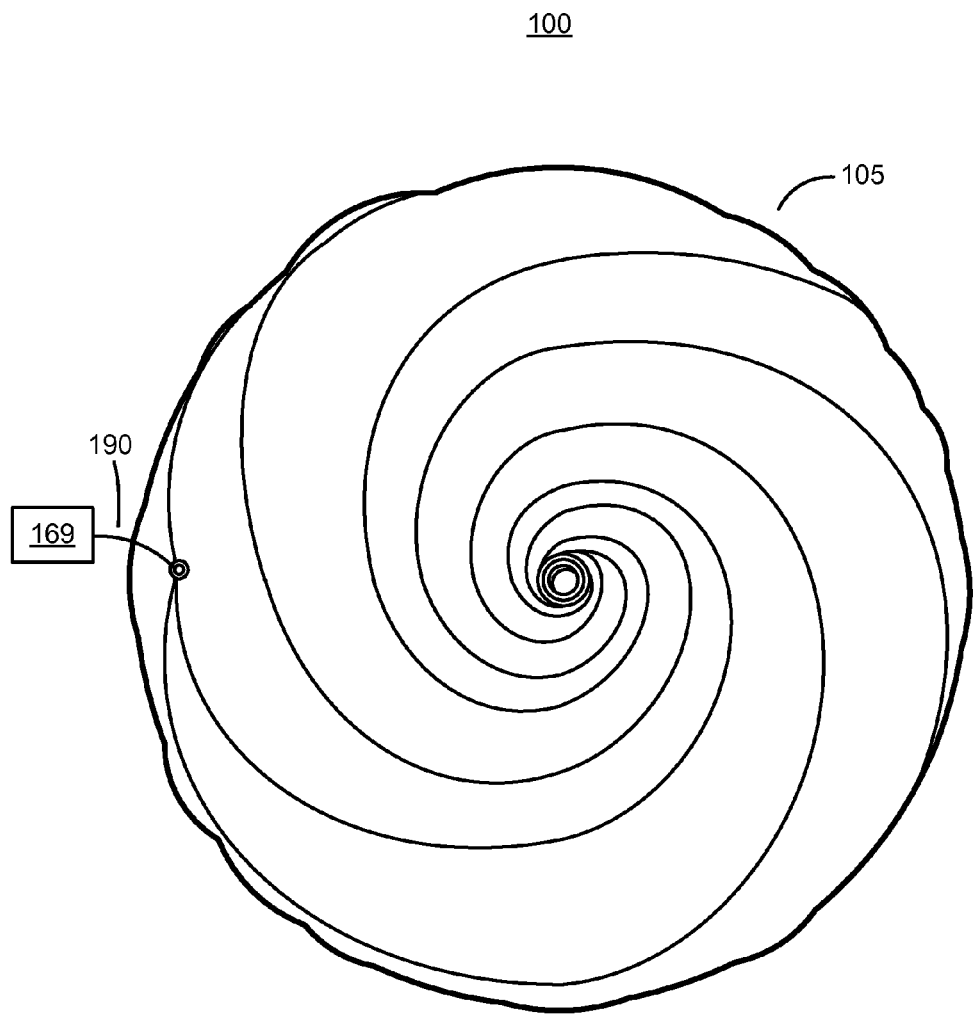
FIGS. 1A-1D depict example devices, in accordance with some example implementations.

FIG. 1A depicts an example system 100 including a cosmetology device 105 which can be placed on the face to provide electrical currents to the face including facial tissue. The cosmetology device 105 may be coupled via line(s) 190 to power and control device 169, which may provide power, current, and the like to the cosmetology device 105.

Although FIG. 1A depicts power and control device 169 separate from cosmetology device 105, the two devices may be included in a single device (for example, cosmetology device 105 may contain power and control device 169).

In some example implementations, the cosmetology device 105 may be of sufficient size to cover the entire face. When this is the case, the cosmetology device 105 does not need to be moved to treat different parts of the face. Moreover, the spiral pattern of the conducting elements of the cosmetology device 105 may facilitate treating a large portion of the face with electrical currents.

Figure 1B:
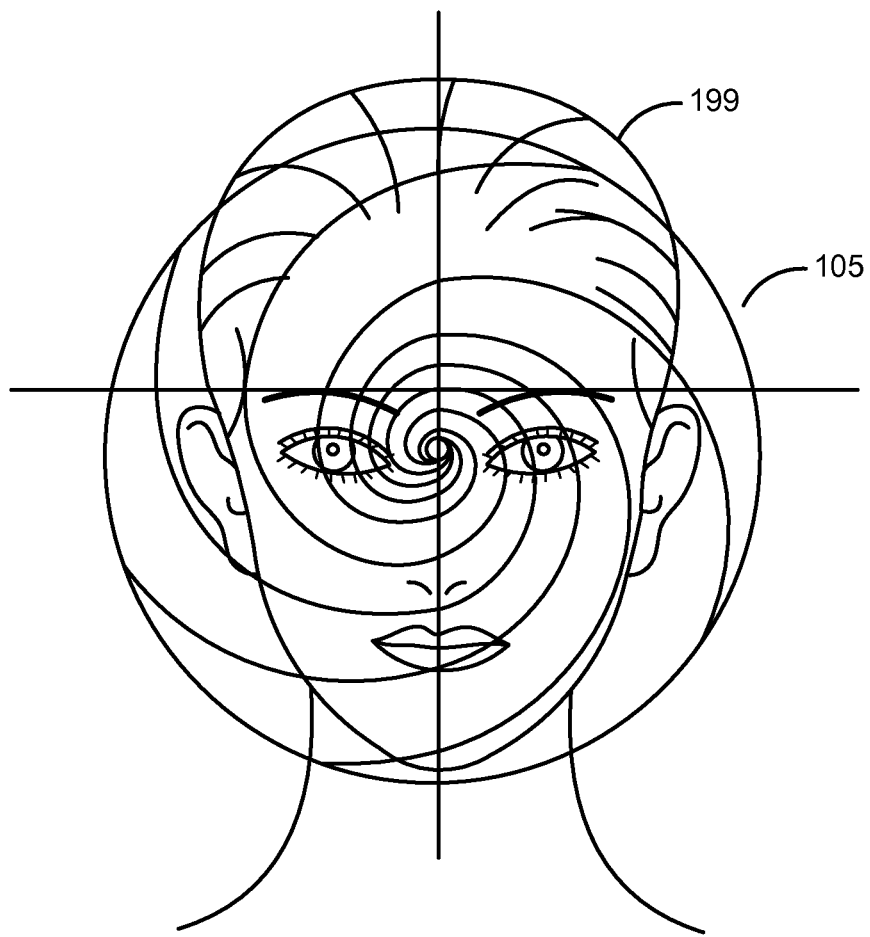

FIG. 1B depicts an example implementation of cosmetology device 105 sized to cover most, if not all, of the face of subject 199. Once the cosmetology device 105 is suitably positioned on the face of the subject to be treated, most, if not all, portions of the face can be treated without repositioning cosmetology device 105.

Figure 1C:
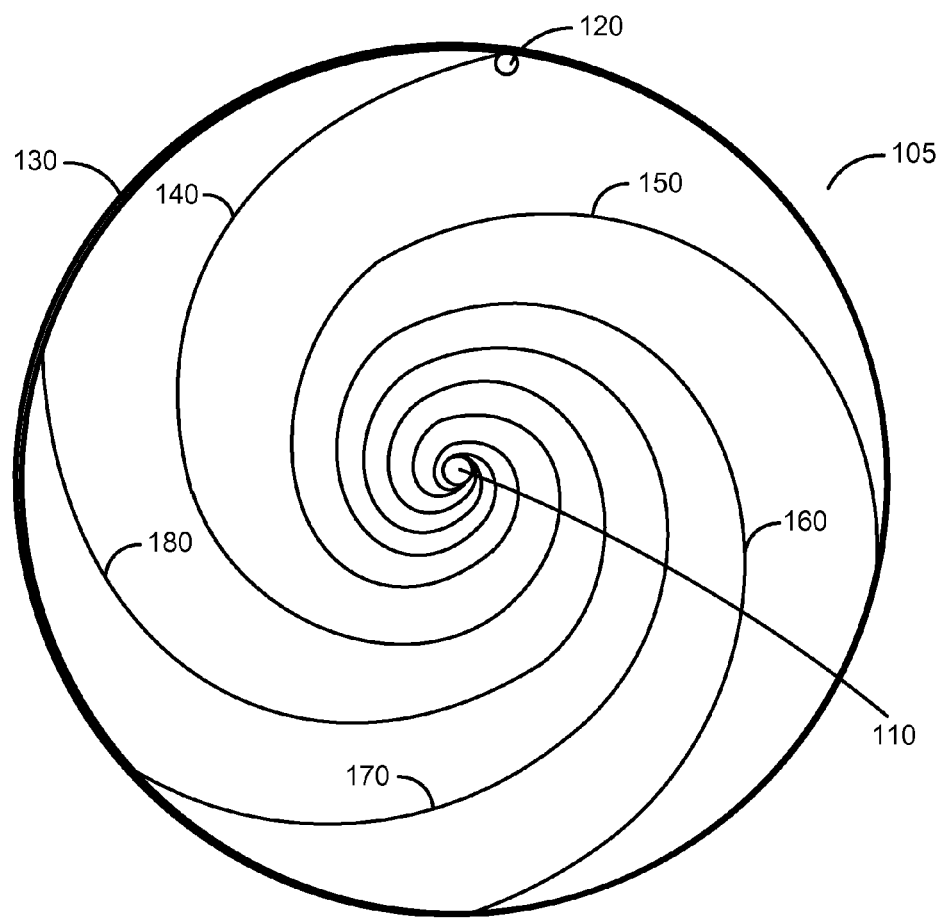

The cosmetology device 105 may include one or more conducting elements that can apply an electrical current, such as a micro-current to the face. FIG. 1C depicts an example of conducting elements having a spiral pattern. For example, the conducting elements 140-180 originate at a center point 110 and then extend spirally outwards towards a perimeter contact ring 130 around the circumference of the device 105. The conducting elements 140-180 may be implemented using for example a wire comprising cooper, aluminum, and/or other conducting material.

The center point 110 may serve as a first electrical contact, and the perimeter contact ring 130 may include a second electrical contact point 120. The first electrical contact 110 and the second electrical contact 120 can be connected to power and control device 169 to enable a flow of micro-currents from the power and control device 169 through lines 190 and the conducting elements 140-180 of the cosmetology device 105.

Power and control device 169 can include a power source, a controller, a waveform generator, a processor, a memory (which may comprise computer-program code to provide the desired control), a user interface, and other suitable components to allow controlling the application of the currents to the conducting elements 140-180. For example, the power and control device 169 may control the intensity of the current, such as the amount of current in amps applied, a duration of the application, and a pattern (for example, a pattern defining what portions of the face should receive electrical stimulation and when that should occur). This control may be preprogrammed and/or user selectable.

The power and control device 169 may produce micro-current to be carried by all of the conducting elements 140-180 simultaneously, such that multiple areas in the cosmetology device 105 are activated and many areas in the face beneath the mask are stimulated. For example, the area around the nose can be stimulated at the same time as the forehead, cheeks, and chin. Alternatively or additionally, power and control device 169 may produce current in a pulsed manner, such that stimulation begins in one region and moves to another. In such cases, the micro-current can be applied to the area around a first region, such as the nose, and then radiate outwards towards other regions, such as the outer edge of the forehead, temple, and bottom of the chin or vice versa, although other stimulation patterns may be used as well. In other implementations of the cosmetology device 105, micro-current can be applied to the mask in zones, such that the forehead is stimulated separately from the cheeks, and that part separately from the chin. Power and control device 169 may apply different levels of micro-currents to different zones. Also, power and control device 169 may vary the time micro-currents are applied to different zones/regions. In some example implementations of the cosmetology device, the mask can include sensors, contacts, and the like to provide feedback by which the cosmetology device can vary the dose of the micro-current.

The cosmetology device 105 may require an intermediate layer between the mask and the underlying face to properly convey current to the skin and tissues of the face. The intermediate layer can be a layer that is applied, such as a gel or cream applied to the face. Alternatively or additionally, the intermediate layer can be a separate implement, such as thin cloth that in impregnated with a conducting fluid or has conductive properties, such that it can cause electrical stimulus of the face as directed by the current flowing the cosmetology device 105. Referring to FIG. 1A, the cosmetology device 105 may be implemented as a pillow, a mask, pad, or other structure capable of carrying the conducting elements 140-180 and being applied to the face. When this is the case, a fluid may be sprayed or otherwise applied to for example the face or pillow to allow the currents being carried by the conducting elements to also traverse facial tissue. Although the examples refer herein to micro-currents, the reference to micro-currents also includes the electromagnetic energy which emanates from conducting elements 140-180 when carrying micro-currents. This electromagnetic energy may also be carried into the face and its tissue as well to provide stimulation, palliative, and/or other effects.

Referring again to FIG. 1C, it shows a view of cosmetology device 105 including conducting elements 140-180 having a spiral pattern, which may provide micro-currents to a large area.

Although FIG. 1C depicts a spiral of the form of a logarithmic spiral, other types of spirals including Archimedean, hyperbolic, and/or any other type of curved structure which winds around a fixed center point (on for example a given plane) at a continuously increasing or decreasing distance from the center point.

The cosmetology device 105 may, as noted, include a fabric outer layer and/or may include a suitable filling to weigh the device 105 onto a surface to be treated so that the spiral conducting elements 140, 150, 160, 170, 180 can impart current and/or other energy to the area to be treated. The cosmetology device 105 may have more than one surface, and at least one surface may be a working surface configured to contact a subject's face or other tissue treated. On the working surface seen in FIG. 1C, the first electrical contact 110 is located medially (e.g., near the center of the working surface), and the second electrical contact 120 is located lateral the perimeter of the working surface, such as on the outer perimeter ring 130.

Each of the conducting elements 140, 150, 160, 170, 180 has a proximal end (also referred to herein as a "head portion") electrically coupled to the first electrical contact 110. And, each of the conducting elements 140, 150, 160, 170, 180 has a distal end (also referred to herein as a "base portion") electrically coupled to the second electrical contact 120 located on the outer perimeter ring 130. As such, an electrical current is able to flow from the power and control line 169, one of the lines 190, first electrical contact 110, and through each of the conducting elements 140, 150, 160, 170, 180 coupled to second electrical contact 120 (and outer perimeter ring 130). The second electrical contact 120 coupled to another one of the lines 190 provides a return path to power and control device 169. Power and control device 169 may thus provide power and control the quantity of power (and/or current, voltage, and the like) applied to the conducting elements 140, 150, 160, 170, 180.

When conducting elements 140, 150, 160, 170, 180 are placed on, or proximate to, a treatment area, such as the face or other tissue, the current flowing (and/or the corresponding electromagnetic energy) through each of the conducting elements 140, 150, 160, 170, 180 can, in some implementations, stimulate the area directly beneath, and to some degree adjacent to, it.

Although FIG. 1C depicts the conducting elements 140-180 sharing common contacts 110 and 120/130, each of the conducting elements 140, 150, 160, 170, 180 may have separate connections to a power source, such as power and control 169.

Moreover, although the above description describes the flow of current from the center of the working surface outwards, other flow patterns may be used as well, such as from the perimeter of the working surface towards the center.

Though the cosmetology device 105 is shown as a substantially circular mechanism including spiral conducting elements, the cosmetology device 105 may have other shapes as well.

Figure 1D:
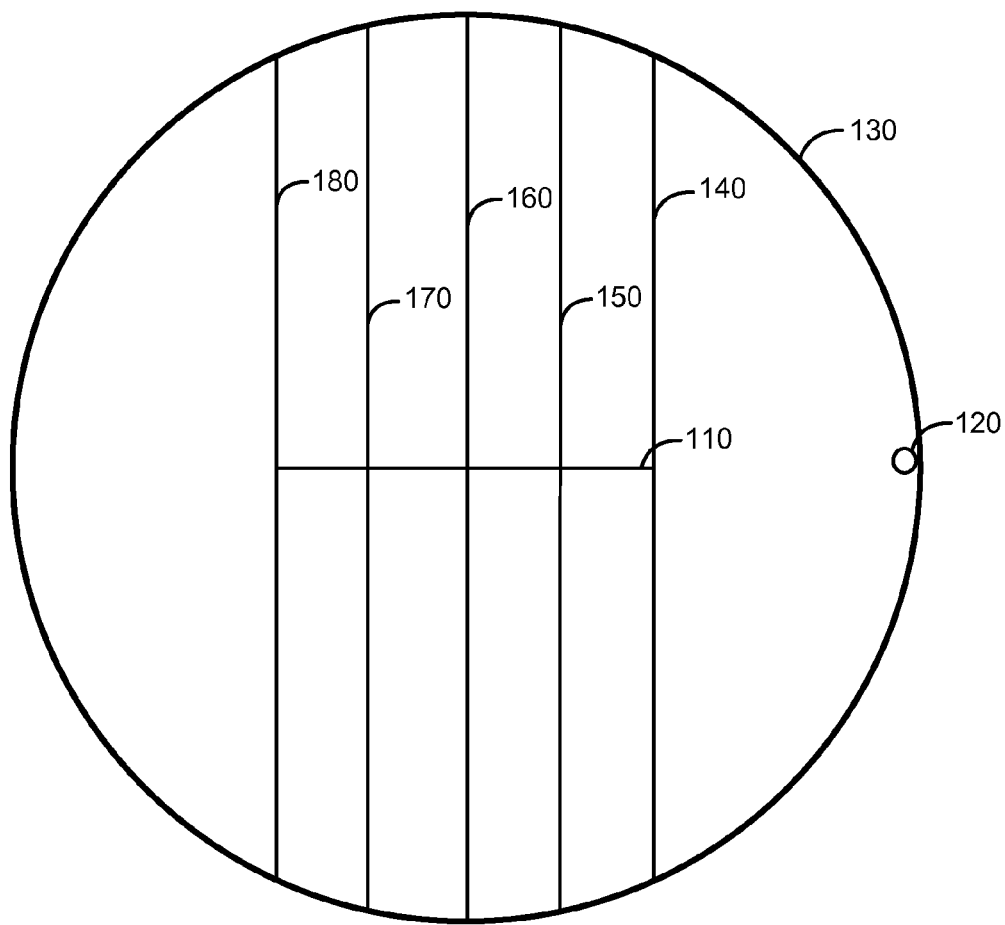
Figure 2B:
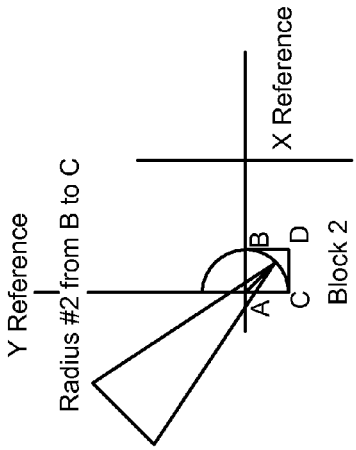
Figure 2D:
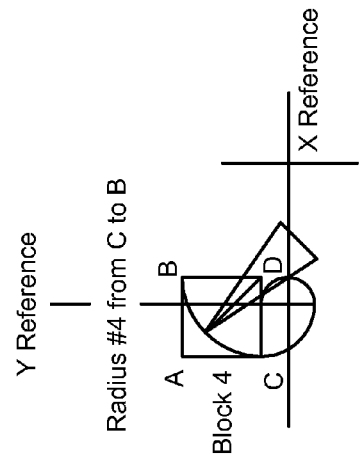
Figure 2A:
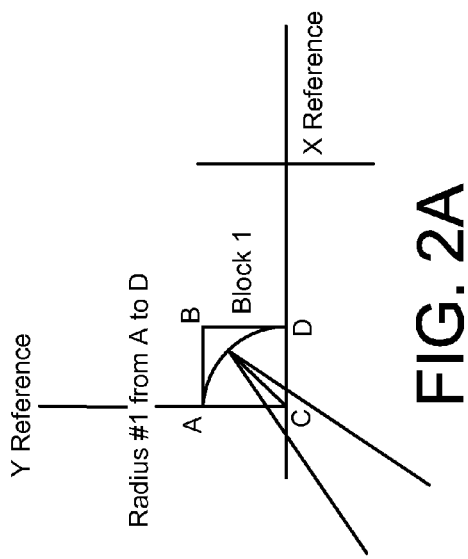
Figure 2C:
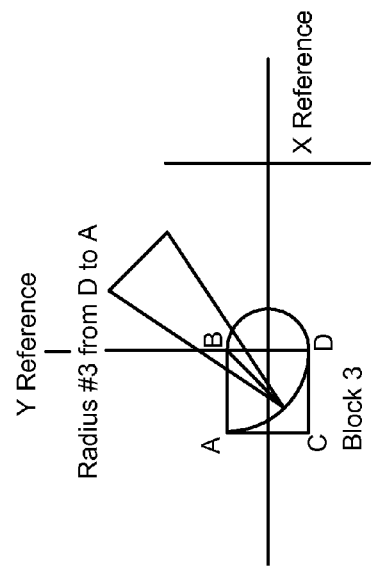
Figure 2I:
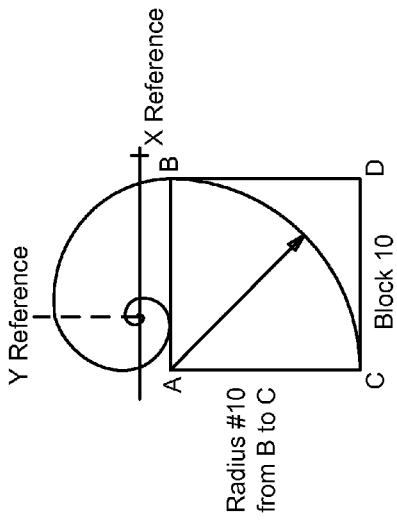
Figure 2J:
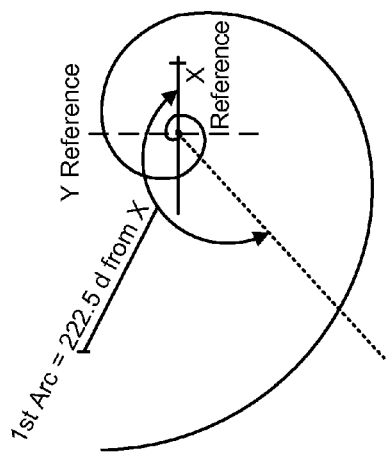
Figure 2K:
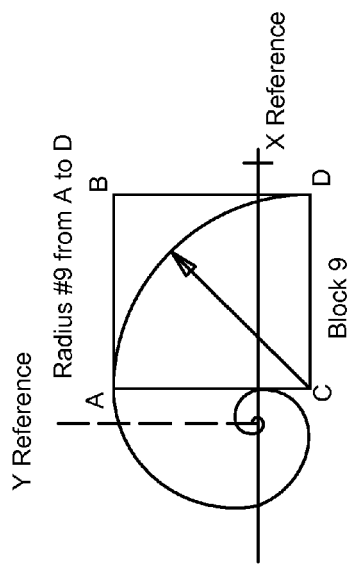
Figure 2L:
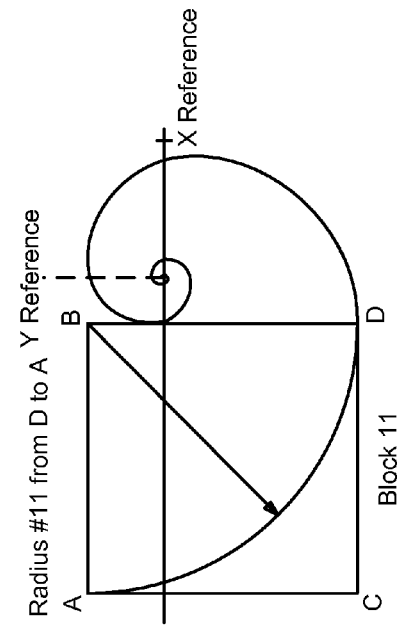

FIG. 1D depicts an example of conducting element having a striated or striped pattern. Conducting elements 140-180 are shown aligned as straight lines, parallel to each other across the cosmetology device 105. Each conducting element 140-180 may connect at its midpoint to the center point line 110 which may serve as the first electrical contact. As in the cosmetology device 105 shown in FIG. 1C, a perimeter contact ring 130 may be situated along the circumference of the cosmetology device 105. The conducting elements may extend from the center point 110 towards the perimeter contact ring 130. The perimeter contact ring may include a second electrical contact point 120. Both the center point line 110 and the second electrical contact point 120 may connect to external power and control devices 169 through lines 190 (shown in FIG. 1A) to enable a flow of micro-current across the face of a user. The conducting elements 140-180 may be spaced any suitable distance, so as to avoid short-circuiting of the cosmetology device 105 while applying current to the desired portions of a user's face or other location on the body. The cosmetology device 105 may also include more conducting elements than shown in FIG. 1D. In some embodiments, the conducting elements may cover the entire contact surface of the cosmetology device 105.

A grid pattern may be formed with the conducting elements in some embodiments with an ordinate and an abscissa. In such embodiments, there may be more than one center point line, for example one for the ordinate and one for the abscissa. The conducting elements that are parallel to the ordinate may connect to the same perimeter contact ring as the conducting elements that are parallel to the abscissa. In some embodiments, the conducting elements that are parallel to the ordinate may connect to a different perimeter contact ring from perimeter contact ring that connects to the conducting elements that are parallel to the abscissa. In embodiments where there are two or more perimeter contact rings in the cosmetology device, differing amounts of current may be applied to different sets of conducting elements. For example, in a grid pattern of conducting elements with two different perimeter contact rings, the conducting elements parallel to the ordinate may be held at one current value or pattern of current fluctuation, while the conducting elements parallel to the abscissa may be held at a second current value or pattern of current fluctuation. In such a configuration, when the conducting elements parallel to the ordinate have one pattern of current fluctuation applied, the conducting elements parallel to the abscissa may have the same pattern of current fluctuation applied, but offset in timing, intensity, or both.

The conducting elements 140, 150, 160, 170, 180 can be made of the aforementioned metals, as well as electrically conductive paint, electrically conductive composite materials, including composite wires, braid, and the like. Other conductive material includes organic compounds, such as glycine, and compounds or mixtures including organic compounds. The conducting elements 140, 150, 160, 170, 180 can be wire (e.g., a solid wire, stranded wire, braided wire, wire weave), a conductive tape, a conductive thread, a conductive yarn, a conductive paint, and the like.

The cosmetology device 105 can be any suitable size. For treating a human face, the device can be, for example, 24 centimeters (cm) in length, 16.5 cm in height, and 4.5 cm in depth, although other sizes may be realized as well.

The description above describes embodiments of a cosmetology device in which the conductive elements, 140, 150, 160, 170, 180, are connected to a common center, or proximal end, contact point and a common outer, or distal end, contact point. However, it should be noted that each conductive element, 140, 150, 160, 170, 180, can be electrically connected to a different electrical circuit, such that a different current can be carried on each conductive element at different times, or the same current at different times, such as in an alternating pattern. Alternatively, two or more conductive elements of a cosmetology device can connect to the same electrical circuit, with the cosmetology device having two or more electrical circuits.

FIGS. 2A-2L show how the pattern of the conducting elements 140, 150, 160, 170, 180 shown in for example FIG. 1C may be derived. Each conducting element forms a spiral, and each spiral originates from approximately the same point and is offset from the adjacent spirals by 222.5 degrees, although other angles may be used as well.

Figure 3:
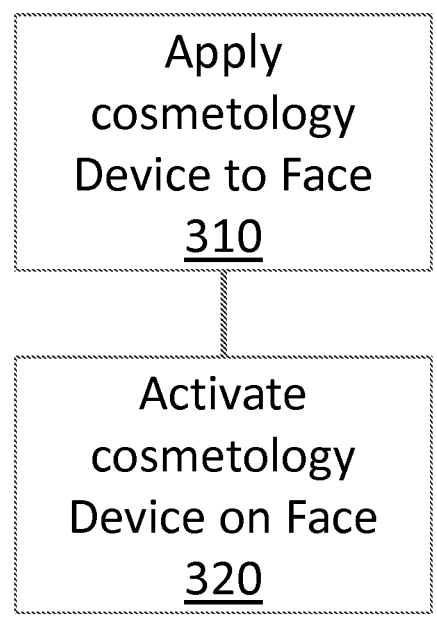
FIG. 3 depicts an example process for treating a subject using a device disclosed herein.

FIG. 3 depicts an example process for treating a subject using the cosmetology device disclosed herein.

At 310, the cosmetology device may be applied to the area being stimulated, treated, and/or the like. For example, cosmetology device 105 may be applied directly to a subject's face. This application may, in some implementations, include applying a conductive fluid to the face or cosmetology device 105 to enhance electrical coupling between the cosmetology device 105 and the face/tissue. This coupling may enable micro-current and other energy to be propagated into the face/tissue.

At 320, the cosmetology device may be activated. For example, the power and control device 169 may apply current (or, for example, voltage, energy, and/or the like) to one or more conductive elements 140-180, and this power may cause a micro-current to flow into one or more conductive elements 140-180. When this is the case, the face/tissue may also experience stimulation and/or other effects based on at least the micro-current flow.

In some implementations, the cosmetology device disclosed herein can be used in a variety of methods, for example to treat the face of a human patient. The methods can be to treat acne by reducing the severity or amount of acne; to improve skin tightness; to increase skin smoothness; to reduce the appearance or formation of scar tissue; to reduce the contrast or size of spots; to reduce the rate of aging; or any combination thereof. The device and system can be used with direct current, alternating current, current applied in wave forms, such as sine waves, saw-tooth waves, square waves, at a constant current, pulsed current, or any other suitable pattern of varying current. Variations in the patterns of the current waveform used and the conducting elements can vary the treatment applied to an area, and methods using the devices and systems described herein can include those to stimulate skin tightening, to tone muscle, to balance human body chakras, to increase physical healing, to provide human body bio-feedback, and any suitable combination thereof.

The devices and systems described herein can be used to treat other parts of the human body, besides the face, including the neck, back, décolletage, arms, lower back, abdomen, legs, or any combination thereof.

The devices, systems, and methods herein can include a device body that accommodates the application of light, sound, odor, various temperatures, variations in pressure across a surface, and the like. The application of light can be accomplished using light emitting components, such as light emitting diodes (LEDs). Sound can include simple vibrations or tones, as well as combinations of notes or even complex melodies and songs. Sounds can be applied using simple vibratory devices or component or by using systems that include amplifying components, such as speakers. Odor can be included in the devices and systems described herein, and thus included in the methods. Aroma therapy odors can be applied to the devices either through the use of agents such as essential oils, as needed, or by the used of components infused with particular odors. Components that inherently have odor, such as particular spices or types of plant material, can also be used. The device can have compartments, pockets, or recesses into which odor components can be added. Odors can also be added to the surface of the device, such as to the device body. Temperature can be controlled by including resistive elements to impart heat and/or components for thermoelectric cooling, such as Peltier cooler components. The device, systems, and methods described herein can be used with the application of increased pressure to selected areas that are simultaneously being treated with electrical stimulation, such as the stimulation of pressure points. The pressure applied to selected areas can also be decreased while simultaneously being treated with electrical stimulation, by, for example, localized exposure to suction or a vacuum.

Additionally, the devices, systems, and methods for applying current to a large area can be compatible with the application of chemicals or other substances to a surface while concurrently applying electrical stimulation. In the case of applying electrical stimulation to a part of the human body, the device can be configured to be used with topical agents, such as creams, gels, oils, lotions, or solutions, that deliver medical compounds, herbal remedies, homeopathic mixtures, and the like. In some cases, the device can include repositories or reservoirs which can hold such topical agents and conduits, pores, membranes, and the like, that can allow for measured delivery of a topical agent over time. The delivery of the topical agent can also be manual and occur by applying a material infused with the topical to the surface underneath the device. Movement, or flow, including delivery of the topical agent, can be activated by the application of current to the surface, or it can be actuated by manipulation of separate buttons, switches, toggles, or mechanisms.

The devices, systems, and methods for electrical stimulation described herein can also have components that are consumable. That is to say that some components can be disposable. For example, some or all of the portions of the electrical stimulation delivering device can be disposed of after a number of uses, after a single use, or with each patient.

Though the devices, systems, and methods are described primarily in the context of delivering micro-current therapy to human faces, it should be recognized that such devices, systems, and methods can be used with various types of stimulation, including higher or lower ranges of electrical current, sonic stimulation that can be activated electronically, and the like. Additionally, the devices, systems, and methods described can also be used to apply electrical therapy to different areas, such as other parts of the human body, to animal bodies, or to other surfaces or volumes with surfaces that could benefit from such stimulation.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A cosmetology device comprising:
a proximal end contact point;
an distal end contact point; and
a plurality of spiral conducting elements radiating from an outer ring including the distal end contact point to a central region including the proximal end contact point, wherein each of the plurality of spiral conducting elements includes a tip portion electrically coupled to the proximal end contact point, and wherein each of the plurality of spiral conducting elements includes a base portion electrically coupled to the outer contact ring to form at least one electrical circuit configured to carry a micro-current.

2. The cosmetology device of claim 1, wherein each of the plurality of spiral conducting elements is offset from an adjacent spiral conducting element by a predetermined angle.

3. The cosmetology device of claim 1, wherein each of the plurality of spiral conducting elements is offset from an adjacent spiral conducting element by an angle of about 222.5°.

4. The cosmetology device of claim 1, wherein the plurality of conducting elements comprise two or more conducting elements.

5. The cosmetology device of claim 1, wherein the plurality of conducting elements comprise at least one of a logarithmic spiral, an Archimedean spiral, a hyperbolic spiral, and a spiral having a curved structure which winds around a fixed center point at a continuously increase or decreasing distance from the proximal end contact point.

6. The cosmetology device of claim 1, further comprising a fabric outer layer onto which the plurality of conducting elements are attached.

7. The cosmetology device of claim 1, wherein the cosmetology device comprises a working surface, the working surface including the plurality of conducting elements.

8. The cosmetology device of claim 7, wherein the working surface is configured to contact a subject's face or other tissue to be treated.

9. The cosmetology device of claim 1, wherein the plurality of conducting elements comprise at least one of a conductive tape, a conductive thread, a conductive yarn, a conductive paint, or a wire.

10. The cosmetology device of claim 1, further comprising a power source and a controller in electrical contact with the proximal end contact point and the distal end contact point.

11. The cosmetology device of claim 1, wherein the plurality of spiral conducting elements radiating from the outer ring including the distal end contact point to the central region are on the same plane.

12. The cosmetology device of claim 1, wherein the micro-current flows at least through the proximal end contact point, the plurality of spiral conducting elements, and the outer ring.

13. A cosmetology device comprising:
a center contact line connected to a first electrical contact;
an outer contact point in electrical contact with a perimeter contact ring that is situated along the circumference of the cosmetology device; and
a plurality of conducting elements, each conducting element extending across a working surface of the cosmetology device, wherein:
a first end of each conducting element contacts a first point on the perimeter contact ring;
a second end of each conducting element contacts a second point on the perimeter contact ring; and
a midpoint of each conducting element contacts the center contact line.

14. The cosmetology device of claim 13, wherein the plurality of conducting elements comprise substantially straight lines when the working surface is flat.

15. The cosmetology device of claim 13, wherein the plurality of conducting elements are aligned in one direction and are substantially parallel to each other.

16. The cosmetology device of claim 13, wherein the plurality of conducting elements are arranged in a grid pattern.

17. The cosmetology device of claim 16, further comprising a second center contact line.

18. The cosmetology device of claim 13, wherein the working surface comprises a fabric outer layer onto which the plurality of conducting elements are attached.

19. The cosmetology device of claim 18, wherein the working surface is configured to contact a subject's face or other tissue to be treated.

20. The cosmetology device of claim 13, wherein the plurality of conducting elements comprise wire comprising copper, aluminum, other conducting material, or any combination thereof.

21. The cosmetology device of claim 13, further comprising a power source and controller in electrical contact with the center contact point and the outer contact point.

22. A method comprising:
applying, to a portion of a face, a cosmetology device for treating the portion, wherein the device includes a center contact point, an outer contact point, and a plurality of spiral conducting elements radiating from an outer ring including the outer contact point to a central region including the center contact point, wherein each of the plurality of spiral conducting elements includes a tip portion electrically coupled to the center contact point, and wherein each of the plurality spiral conducting elements includes a base portion electrically coupled to the outer contact ring to form at least one electrical circuit configured to carry a micro-current into the cosmetology device; and
energizing the cosmetology device to allow energy to radiate into the portion of the face.

23. A method comprising:
applying to a portion of a face, a cosmetology device for treating the portion, wherein the device comprises a center contact line connected to a first electrical contact, an outer contact point in electrical contact with a perimeter contact ring that is situated along the circumference of the cosmetology device, and a plurality of conducting elements, each conducting element extending across a working surface of the cosmetology device, wherein a first end of each conducting element contacts a first point on the perimeter contact ring, a second end of each conducting element contacts a second point on the perimeter contact ring, and a midpoint of each conducting element contacts the center contact line.

\* \* \* \* \*